United States Patent [19]

Simmons

[11] 4,316,858

[45] Feb. 23, 1982

[54] PREPARATION OF ARYLPHOSPHINIC ACIDS

[75] Inventor: Kirk A. Simmons, Scarsdale, N.Y.

[73] Assignee: Stauffer Chemical Company, Westport, Conn.

[21] Appl. No.: 248,102

[22] Filed: Mar. 27, 1981

[51] Int. Cl.³ ............................................. C07F 9/28
[52] U.S. Cl. ........................................... 260/502.4 R
[58] Field of Search .................................... 260/502.4

[56] References Cited

U.S. PATENT DOCUMENTS

| | | | |
|---|---|---|---|
| 2,137,792 | 11/1938 | Woodstock | 260/502.4 R |
| 2,594,454 | 4/1952 | Kosolapoff | 260/502.4 R |
| 2,632,018 | 3/1953 | Kosolapoff | 260/502.4 R |
| 3,903,208 | 9/1975 | Hofer et al. | 260/502.4 R |
| 3,974,217 | 8/1976 | Miles | 260/543 P |

OTHER PUBLICATIONS

Higgins et al., "J. Am. Chem. Soc.", vol. 77 (1955), pp. 1864–1866.
Frank, "Chemical Reviews", vol. 61 (1961), pp. 389–424.
Kosolapoff, "Organophosphorus Compounds", pp. 43–46 and 128.

*Primary Examiner*—Joseph E. Evans
*Attorney, Agent, or Firm*—William C. Gerstenzang

[57] ABSTRACT

Arylphosphinic acids are prepared by reacting an aryl compound with phosphorus trichloride in the presence of aluminum chloride to form a first reaction product, adding the first reaction product to water to precipitate a second product, dissolving the second product in an alkali metal hydroxide solution which is then treated with carbon dioxide to precipitate aluminum hydroxide, which is then removed; the remaining solution is then acidified and the arylphosphinic acid product recovered therefrom.

11 Claims, No Drawings

PREPARATION OF ARYLPHOSPHINIC ACIDS

BACKGROUND OF THE INVENTION

The present invention relates to an improved process for the preparation of arylphosphinic acids. More particularly, the present invention relates to a process for preparing arylphosphinic acids by an aluminum chloride catalyzed reaction of an aryl compound with phosphorus trichloride in which the prior art difficulties associated with separating the product from aluminum chloride complexes are effectively solved.

Arylphosphinic acids are compounds which are useful as catalysts and stabilizers in nylon synthesis and are also useful as intermediates in the production of a wide variety of useful compositions, such as pesticides, fuel and oil additives and the like.

One of the best known methods for preparing these compounds involves the reaction of an aryl compound with phosphorus trichloride in the presence of aluminum trichloride to produce an aryl phosphonous dichloride, which is then hydrolyzed to produce the acid. Unfortunately, however, the aluminum chloride forms certain complexes during the process, which makes recovery of the final product difficult.

A method suggested by the prior art for circumventing the problems presented by the aluminum chloride complexes involves the addition of phosphorus oxychloride to the reaction mixture to form an aluminum chloride-phosphorus oxychloride complex, which settles from the reaction mixture, thereby facilitating recovery of the aryl phosphonous dichloride product. While this method is helpful, it is less than desirable because large amounts of phosphorus oxychloride are required and the remaining aluminum chloride-phosphorus oxychloride precipitate is a reactive waste product which can be difficult to dispose of. In addition, not all of the aluminum complex is removed, and the small amount remaining can lead to the formation of an emulsion during a subsequent reaction of the aryl phosphonous dichloride with water, which further complicates the process.

U.S. Pat. No. 3,974,217 teaches the preparation of alkoxy and alkylthio substituted phenyl phosphonous dichlorides by reacting an appropriate substituted aryl compound with phosphorus trichloride in the presence of stannic chloride or titanium tetrachloride. It would appear, however, that this method would be less than successful with compounds not having the activating alkoxy or alkylthio substituents, since the catalysts used are less effective Friedel-Crafts catalysts.

A need therefore exists for a method by which arylphosphinic acids can be prepared from appropriate aryl compounds and phosphorus trichloride using aluminum chloride as catalyst without encountering the prior art difficulties occasioned by the formation of aluminum chloride complexes.

SUMMARY OF THE INVENTION

It has now been found that arylphosphinic acids can be prepared from appropriate aryl compounds and phosphorus trichloride, using aluminum chloride catalyst, without encountering the prior art difficulties occasioned by the presence of aluminum chloride complexes by adding the initial reaction product to water to form a precipitate, dissolving the precipitate in an aqueous alkali metal hydroxide solution, treating the solution with carbon dioxide to precipitate aluminum hydroxide, removing the aluminum hydroxide and acidifying the remaining solution to form the arylphosphinic acid product and recovering same.

DETAILED DESCRIPTION OF THE INVENTION

In accordance with the present invention there is provided a process for the preparation of arylphosphinic acids comprising reacting an aryl compound susceptible to electrophilic ring substitution with phosphorus trichloride in the presence of aluminum chloride to form a first reaction product, adding the first reaction product to water to precipitate a second reaction product and recovering the precipitate.

The precipitate, which is thought to be an aluminum salt of the arylphosphinic acid, is then dissolved in an alkali metal hydroxide solution. The alkali metal hydroxide solution is then treated with carbon dioxide to precipitate aluminum hydroxide. The aluminum hydroxide precipitate is then removed from the solution, and the remaining solution acidified to form the arylphosphinic acid. The arylphosphinic acid can then be recovered from the acidified solution by a standard workup technique.

The aryl compounds which are used in the practice of the present invention are those which are susceptible to electrophilic ring substitution. They include, but are not limited to compounds represented by the formula:

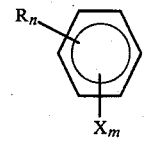

wherein each R is independently hydrogen, alkyl having from 1 to about 12 carbon atoms, alkoxy having from 1 to about 6 carbon atoms, alkylthio having from 1 to about 6 carbon atoms, aryl or substituted aryl having from 6 to about 12 carbon atoms or cycloalkyl having from 3 to about 8 carbon atoms; n represents a number ranging from 0 to 5; X represents hydrogen or a halogen and m represents a number ranging from 0 to 5. Preferred aryl compounds are those wherein R is alkyl or alkoxy having from 0 to about 4 carbon atoms.

Exemplary aryl compounds include benzene, toluene, naphthalene, p-xylene, p-chlorotoluene, 1,3,5-trimethylbenzene and biphenyl.

Heterocyclic compounds, such as thiophene can be used in place of the aryl compound, and compounds having more than one benzene ring such as diphenylmethane and polyphenyl ethers can also be used.

A particularly preferred aryl compound is p-xylene.

The reaction between the aryl compound and $PCl_3$ is preferably carried out in an excess of phosphorus trichloride. The amount of phosphorus trichloride charged therefore ranges from about 1 to about 5 moles per mole of aryl compound charged, and preferably from about 2 to about 4 moles phosphorus trichloride per mole aryl compound.

It is also preferred to use relatively large amounts of the aluminum chloride catalyst. The amount of aluminum chloride charged therefore ranges from about 1 mole aluminum chloride per mole aryl compound to about 5 moles aluminum chloride per mole aryl compound, although a range of from about 1 to about 1.5 moles aluminum chloride per mole aryl compound is preferred. The process is operable at lower or higher catalyst ratios, but with lower catalyst ratios conversion to the desired product may not be as complete as desired, while with higher ratios unwanted by-products resulting from multiple substitution on phosphorus could result.

The reaction between the aryl compound and phosphorus trichloride is generally conducted at a temperature ranging from about 20° C. to about 100° C. or higher, although a temperature ranging from about 50° C. to about 75° C. is preferred. The subsequent reaction of the first reaction product with water can be conducted at room temperature or at an elevated temperature, but a reduced temperature (i.e., between about 0° C. and about 20° C.) is preferred.

The alkali metal hydroxide solution in which the second reaction product is dissolved is preferably an aqueous solution of sodium hydroxide, potassium hydroxide or calcium hydroxide, although sodium hydroxide is particularly preferred. The concentration of the solution is not critical, but a concentration of about 5% alkali metal hydroxide by weight of solution is preferred. At concentrations below about 5%, the second reaction product may not all be dissolved, while at concentrations above about 5%, more carbon dioxide will be required in the next step than would otherwise be.

While the second reaction product can be added directly to an alkali metal hydroxide solution and dissolved, it is preferred to dissolve the second reaction product in the alkali metal solution by first suspending the product in water, and then adding a predetermined amount of a concentrated alkali metal hydroxide solution; the predetermined amount being an amount sufficient to dissolve the suspended product.

The resulting solution is then treated with carbon dioxide to precipitate aluminum hydroxide. Preferably, the solution is saturated with carbon dioxide.

While there are various methods available for treating the solution with the carbon dioxide, it is preferred to treat the solution by bubbling carbon dioxide gas though it. This method has the advantage of simplicity, and is self-agitating.

The addition of carbon dioxide to the solution causes the aluminum to precipitate as aluminum hydroxide, which can be easily separated from the remaining solution. One method for removing the aluminum hydroxide consists of filtering it with the use of a filter-aid; while another method consists of removing it with a centrifuge. Other standard separation techniques can also be used effectively.

The remaining solution can then be acidified to form the arylphosphinic acid. While it is preferred to acidify the solution by the addition of concentrated hydrochloric acid thereto, other acids can also be used.

While the pH reached is not a critical factor, it is an important factor in obtaining the most yield from the process. It is therefore preferred to acidify the solution to a pH of about pH 1.0, although this is not critical.

The arylphosphinic acid which is formed can then be removed from the solution by standard work-up techniques. Thus, for example, the arylphosphinic acid can be extracted from the solution with methylene chloride, which can then be evaporated to produce the acid in a relatively pure state.

In order that the present invention be more fully understood, the following example is given by way of illustration. No specific details or enumerations contained therein should be construed as limitations to the present invention except insofar as they appear in the appended claims. All parts and percentages are by weight unless otherwise specifically designated.

EXAMPLE

PREPARATION OF 2,5-DIMETHYLBENZENEPHOSPHINIC ACID

To a flame dried 3-neck 1 liter flask was added in order 107 g. (1.0 mole) p-xylene, 412 g. (3.0 mole) phosphorus trichloride and 160 g. (1.2 mole) anhydrous aluminum chloride. The reaction slurry was slowly heated with stirring to reflux by which time all solids had dissolved. After 2½ hours at reflux the reaction was allowed to cool to room temperature and the volatile components distilled at reduced pressure (ca. 50 mm Hg). About 179 g. of volatile components were recovered. The resulting oil was slowly added to 1 liter of cold water with stirring and the white solid which formed was isolated by filtration, washed with water and air-dried. Yield was 332 g. The solid was suspended in 1000 ml. of water and dissolved by adding 90 ml. of 50% sodium hydroxide. A small amount of solid failed to dissolve (14 g.). The alkaline solution was then saturated with carbon dioxide. Aluminum hydroxide slowly precipitated, and was removed by filtration through a filter-aid. The basic filtrate was washed with a small amount of methylene chloride (ca. 200 ml.) which was discarded. Upon acidification with concentrated hydrochloric acid (200 ml.), the 2,5-dimethylbenzenephosphinic acid separated and was isolated by extraction with methylene chloride (3×250 ml). Drying (MgSO$_4$) and concentrating the organic extract produced 99 g. of the phosphinic acid as an oil which slowly crystallized.

Yield: 60% of theory, mp=77°–79° C.

I claim:

1. A process for the preparation of an aryl-phosphinic acid comprising reacting an aryl compound susceptible to electrophilic ring substitution with phosphorus trichloride in the presence of aluminum chloride to form a first reaction product, adding said first reaction product to water to precipitate a second reaction product, dissolving said second reaction product in an alkali metal hydroxide solution, treating said alkali metal hydroxide solution with carbon dioxide to precipitate aluminum hydroxide, removing said aluminum hydroxide and acidifying the remaining solution to form said arylphosphinic acid product.

2. The process of claim 1 wherein said aryl compound is an aryl compound represented by the structure

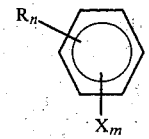

wherein each R is independently hydrogen, alkyl having from 1 to about 12 carbon atoms, alkoxy having from 1 to about 6 carbon atoms, alkylthio having from 1 to about 6 carbon atoms, aryl or substituted aryl having from 6 to about 12 carbon atoms or cycloalkyl having from 3 to about 8 carbon atoms; x represents hydrogen or a halogen, n represents a number ranging from 0 to 5 and m represents a number ranging from 0 to 5.

3. The process of claim 2 wherein said aryl compound is a compound selected from the group consisting of benzene, naphthalene, p-xylene, p-chlorotoluene, 1,3,5-trimethyl benzene and biphenyl.

4. The process of claim 3 wherein said aryl compound is p-xylene.

5. The process of claim 1 wherein the amount of $PCl_3$ present during the reaction between said aryl compound and $PCl_3$ ranges from 1 to about 5 moles $PCl_3$ per mole aryl compound.

6. The process of claim 5 wherein the amount of aluminum chloride present during said reaction between said aryl compound and said $PCl_3$ ranges from 1 to about 5 moles aluminum chloride per mole aryl compound.

7. The process of claim 1 wherein said alkali metal hydroxide solution is an aqueous solution of sodium hydroxide.

8. The process of claim 7 wherein the concentration of sodium hydroxide in said solution is about 5% by weight.

9. The process of claim 1 wherein said treatment of said alkali metal hydroxide solution with carbon dioxide is accomplished by bubbling carbon dioxide gas through said solution until substantially all of the aluminum present in said solution has been precipitated as aluminum hydroxide.

10. The process of claim 1 wherein said remaining solution is acidified by the addition thereto of hydrochloric acid.

11. The process of claim 10 wherein said hydrochloric acid is added in an amount sufficient to reduce the pH of said remaining solution to about pH 1.0.

* * * * *